(12) United States Patent
Alonso-Caplen et al.

(10) Patent No.: US 7,687,240 B2
(45) Date of Patent: Mar. 30, 2010

(54) PROCESS FOR INCREASING RSV SURFACE GLYCOPROTEIN YIELDS USING A MUTANT STRAIN OF RSV

(75) Inventors: Firelli Alonso-Caplen, Tappan, NY (US); Mark Cutler, Bloomingdale, NJ (US); Mirelli Fino, Stamford, CT (US); Earl Pursell, Valley Cottage, NY (US); Robert Repetto, Garrison, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 558 days.

(21) Appl. No.: 10/549,533

(22) PCT Filed: Mar. 17, 2004

(86) PCT No.: PCT/US2004/008028

§ 371 (c)(1),
(2), (4) Date: Sep. 15, 2005

(87) PCT Pub. No.: WO2004/083397

PCT Pub. Date: Sep. 30, 2004

(65) Prior Publication Data

US 2006/0171955 A1    Aug. 3, 2006

Related U.S. Application Data

(60) Provisional application No. 60/455,537, filed on Mar. 18, 2003.

(51) Int. Cl.
*C12Q 1/70* (2006.01)
*G01N 33/567* (2006.01)
*C12N 7/04* (2006.01)

(52) U.S. Cl. .................. 435/7.21; 435/5; 435/236

(58) Field of Classification Search ............... None
See application file for complete search history.

(56) References Cited

U.S. PATENT DOCUMENTS 5,922,326 A    7/1999    Murphy et al.

OTHER PUBLICATIONS

Hancock et al. Serum Neutralizing Antibody Titers of Seropositive Chimpanzees Immunized with Vaccines Coformulated with Natural Fusion Attachment Proteins of Respiratory Syncytial Virus. Journal of Infectious Diseases, 2000, vol. 181, pp. 1768-1771.*
Firestone et al. Nucleotide sequence analysis of the respiratory syncytial virus subgroup A cold-passaged (cp) temperature sensitive (ts) cpt-248/404 live attenuated virus vaccine candidate. Virology, 1996, vol. 225, pp. 419-422, Article No. 0618, Short Communication.*
Johnson et al. Prining with Secreted Glycoprotein G of Respiratory Syncytial Virus (RSV) Augments Interleukin-5 Production and Tissue Eosinophilia after RSV Challenge. Journal of Virology, Apr. 1998, vol. 72, No. 4, pp. 2871-2880.*

* cited by examiner

*Primary Examiner*—Robert B Mondesi
*Assistant Examiner*—Sharon Hurt
(74) *Attorney, Agent, or Firm*—Gloria K. Szakiel; J. Darrell Fontenot (57) ABSTRACT

A process for producing isolated and purified respiratory syncytial virus (RSV) fusion (F) and attachment (G) glycoproteins in eukaryotic cell cultures infected with RSV cold-passaged, temperature-sensitive mutant subgroup A2 strain cpts-248/404 results in at least a 5-fold increase in F and G protein yields when compared with the parent A2 strain. Immunogenic compositions comprising the F and/or G protein(s) produced by this process can be formulated for in vivo administration to a host to confer protection against disease caused by RSV.

4 Claims, 2 Drawing Sheets

PROCESS FOR INCREASING RSV SURFACE GLYCOPROTEIN YIELDS USING A MUTANT STRAIN OF RSV

This application is the US national phase of international application PCT/US2004/008028 filed on Mar. 17, 2004, which designated the US and claims priority to US Provisional Application No. 60/455,537, filed Mar. 18, 2003. The entire contents of these applications are incorporated herein by reference.

FIELD OF THE INVENTION

The present invention relates to a method of identifying a respiratory syncytial virus (RSV) strain that produces high yields of RSV surface glycoproteins. The present invention also relates to the subsequent production, isolation and purification of these proteins for their use in immunogenic compositions that are effective in conferring protection against disease caused by RSV.

BACKGROUND OF THE INVENTION

Acute lower respiratory tract disease is the leading contributor to morbidity and mortality in young children throughout the world. Respiratory syncytial virus (RSV) is the most important viral cause of serious lower respiratory tract disease in infants and children worldwide. It is also a significant cause of lower respiratory tract disease in the elderly and those with pre-existing chronic cardiac or lung disease such as cystic fibrosis (CF).

The structure and composition of RSV has been elucidated and is described in detail in the textbook "Fields Virology", ed. by Knipe, D. M. et al., Lippincott Williams & Wilkins, NY (2001), in particular, Chapter 45, pp. 1443-1485, "Respiratory, Syncytial Virus" by Collins, P., Chanock, R. M. and Murphy, B. R.

RSV is an enveloped RNA virus of the family Paramyxoviridae and of the genus *Pneumovirus*. The two major protective antigens of RSV are the envelope fusion (F) and attachment (G) glycoproteins. The F protein is synthesized as a 68 kDa precursor molecule ($F_0$) which is proteolytically cleaved into disulfide-linked $F_1$ (about 48 kDa) and $F_2$ (about 20 kDa) polypeptide fragments. The unglycosylated G protein (about 33 kDa) is heavily O-glycosylated giving rise to a glycoprotein of apparent molecular weight of about 90 kDa. Two broad subtypes of RSV have been defined A and B. The major antigenic differences between these subtypes are found in the G protein while the F protein is more conserved.

Currently, no immunogenic composition to prevent or attenuate RSV-related illness is available. Numerous candidate immunogenic compositions have been tested over the past thirty years but none have been licensed to date. First and second generations of the purified fusion protein (designated PFP-1 and PFP-2) immunogenic composition, an RSV subunit immunogenic composition, have been tested in RSV seropositive children and they have been shown to be safe and reasonably immunogenic.

The purification of the RSV F and G proteins by immunoprecipitation or preparative SDS-PAGE provides only small amounts of protein. Thus, there remains a need for immunogenic compositions effective in conferring protection against disease caused by RSV, and there is also a need for a process that produces high yields of the RSV glycoproteins to meet the demands of all target populations, such as older children and the elderly.

SUMMARY OF THE INVENTION

The present invention provides a method of identifying an RSV strain that produces high yields of RSV F and G glycoproteins. This method comprises providing a eukaryotic cell culture, infecting the culture with a live attenuated RSV A2 strain, and determining the glycoprotein concentration in the infected cell culture, wherein at least a five-fold increase in F and/or G protein concentration is an indication that the attenuated RSV strain produces high yields of RSV F protein and/or G protein when compared with the parent A2 strain. The inventors discovered that the RSV mutant A2 strain cpts-248/404 (ATCC VR 2454) produces more than five times the F protein when grown in, for example, VERO cells at 30° C. than does the parent A2 strain grown at 37° C. See Tables 7 and 8 below.

Also contemplated is a process for producing purified RSV F and/or G protein from eukaryotic cells infected with the RSV mutant strain cpts-248/404. This process comprises growing eukaryotic cells infected with the RSV mutant strain cpts-248/404 in a culture medium, solubilizing the F and/or G protein(s) from the virus infected cell membrane, and isolating and purifying the solubilized F and/or G protein(s).

The isolation and purification can be effected by standard procedures well known to those skilled in the art, including chromatography (e.g., ion exchange, immunoaffinity, and sizing column chromatography), centrifugation, differential solubility, or by any other standard procedure for the purification of proteins.

Also contemplated is a process for producing an immunogenic composition for protecting against disease caused by RSV, wherein said process comprises growing eukaryotic cells infected with the RSV mutant strain cpts-248/404 in a culture medium; solubilizing the F and/or G protein(s) from the virus infected cell membrane; isolating and purifying the solubilized F and/or G protein(s); and bringing an effective amount of said solubilized F and/or G protein(s) into combination or association with a physiologically acceptable carrier.

Also contemplated is the purified RSV F protein produced by this process (designated PFP-3), i.e., in a cell line infected with the RSV cold-passaged, temperature-sensitive mutant subgroup A2 strain cpts-248/404, in yields that are at least five times greater than the yields of RSV F protein produced using the parent A2 strain (PFP-2), thereby making the production of RSV F protein (PFP-3) commercially feasible.

Also contemplated is the purified RSV G protein produced by this process, i.e., in a cell line infected with the RSV cold-passaged, temperature-sensitive mutant subgroup A2 strain cpts-248/404, in yields that are at least five times greater than the yields of RSV G protein produced using the parent A2 strain, thereby making the production of RSV G protein commercially feasible.

Also contemplated is the use of an RSV mutant subgroup A2 strain cpts-248/404 in the preparation of an RSV envelope fusion (F) protein and/or RSV attachment (G) glycoprotein.

Also contemplated is an immunogenic composition comprising, in a physiologically acceptable carrier, an immuno-effective amount of the F protein (PFP-3) provided herein. Each immunogenic composition provided herein can be formulated for in vivo administration to a host, which may be a primate, specifically a human host, to confer protection against disease caused by RSV.

Also contemplated is an immunogenic composition comprising, in a physiologically acceptable carrier, an immuno-effective amount of the G protein provided herein. Each immunogenic composition provided herein can be formulated for in vivo administration to a host, which may be a primate, specifically a human host, to confer protection against disease caused by RSV.

The immunogenic compositions of the invention can be formulated as microparticles, capsules, ISCOMs or liposomes. The immunogenic compositions can further comprise at least one other immunogenic or immunostimulating material, which may be at least one adjuvant or at least one immunomodulator.

The immunogenic compositions provided herein can be formulated to comprise at least one additional immunogen, which conveniently may comprise the other RSV protein (i.e., G in addition to F or F in addition to G), or a human Parainfluenza virus (PIV) protein from PIV-1, PIV-2 and/or PIV-3 such as F and HN proteins. However, other immunogens, such as from Chlamydia, polio, hepatitis B, diphtheria toxoid, tetanus toxoid, influenza, *haemophilus, B. pertussis*, pneumococci, mycobacteria, hepatitis A and *Moraxella* also can be incorporated into the compositions, as polyvalent (combination) immunogenic compositions.

BRIEF DESCRIPTION OF THE DRAWINGS

FIG. 2 shows the capacity of PFP-2 and PFP-3 to generate cell-mediated immune responses in BALB/c mice. BALB/c mice were immunized (intramuscularly) on weeks 0 and 4 with 3 μg F protein from either mutant 248/404 (circles) or A2 (triangles) strains of RSV. The immunogenic compositions were admixed with QS-21 (20 μg/dose). Control mice were immunized by experimental infection with the A2 strain of RSV (filled squares) or received intranasally an equal volume of mock infected HEp-2 cell lysate (open squares). Two weeks after the last immunization the mice were challenged with the A2 strain of RSV. Pulmonary inflammatory cells were isolated by bronchoalveolar lavage five days later and tested directly ex vivo against syngeneic infected (RSV A2, solid lines) or control (dashed lines) targets. There were five mice per group.

DETAILED DESCRIPTION OF THE INVENTION

Up to now, the parent virus strain (A2) has been the source of F protein (PFP-2) for an RSV subunit immunogenic composition. Concerns have been raised, however, regarding the ability to produce quantities of native F protein from the A2 strain of RSV sufficient to meet the demands of all target populations. Based on F protein yields from the parent strain A2, development of a manufacturing-scale process for F protein was not feasible. Surprisingly, F protein production using the RSV temperature-sensitive mutant strain cpts-248/404 resulted in a greater than five-fold increase in F protein (PFP-3) yields as compared with the A2 strain, which made development of a manufacturing-scale process for F protein feasible. Since the use of cpts-248/404 makes F protein production on a large scale more feasible, preclinical efforts focused on demonstrating immunological and biochemical equivalence of F proteins purified from the A2 and mutant cpts-248/404 strains of RSV (see below).

As discussed above, the present invention provides the biochemically purified F protein from the cold-passaged, temperature-sensitive mutant strain cpts-248/404 (PFP-3). This is a cold-passaged strain of RSV A2 (cp-248) that was further attenuated by chemical mutagenesis (5-fluorouracil) in VERO cells. This attenuated strain was found to be 1000-fold restricted in replication compared to wild-type and 100-fold restricted in replication compared to the parent A2 strain at 37° C. The RSV mutant strain cpts-248/404 has been shown to produce greater than five times the F protein levels during infection of VERO cells on microcarriers in a bioreactor at 30° C. when compared with the parent A2 strain grown at 37° C.

The cpts-248/404 virus is grown in any cell line that supports RSV growth, such as, for example, VERO, MRC-5, FRhL, CEF (chicken embryo fibroblast) and PER.C6 cells. The infection process proceeds for about eight days until there is greater than 90% syncytial formation and cellular detachment from the microcarriers. At that time, the infected cell culture is lysed in situ with 0.5% v/v Triton X-100 for 2 hours at 30° C. The lysed cell culture supernatant is clarified by depth filtration followed by ultrafiltration/diafiltration. The diafiltered lysate is applied to an anion exchange column and the flow through fraction, containing the F protein, is collected. The flow through fraction is diafiltered utilizing a spiral wound ultrafiltration module and applied to a cation exchange column. The F protein is eluted with a step gradient of higher ionic strength. The cation exchange pool is diafiltered utilizing an ultrafiltration module and applied to a hydroxyapatite column. The F protein is eluted with a step gradient of higher phosphate concentration and higher pH. Fractions containing F protein are pooled, terminally sterile-filtered, and frozen at −70° C. until formulation.

The current process to purify G protein from cpts-248/404-infected Vero cells starts with the same process as for the F protein purification (PFP-3). Identical to the process for F protein, the infection process proceeds for eight days until there is greater than 90% syncytial formation and cellular detachment from the microcarriers. At that time, the infected cell culture is lysed in situ with 0.5% v/v Triton X-100 for 2 hours at 30° C. The lysed cell culture supernatant is clarified by depth filtration followed by ultrafiltration/diafiltration. The diafiltered lysate is applied to an anion exchange column and the flow through fraction, containing the F protein, is collected. The G protein is retained by the DEAE column and eluted with a step elution to 200-mM NaCl.

The G protein from the DEAE pool is then applied to a boronic acid affinity chromatography column with the boronate ligand 3-aminophenylboronic acid (APBA) utilizing a 9-atom spacer at pH 8.5. The esterification of boronate with 1,2-cis-diol provides the basis for the purification of macromolecules that possess two hydroxyl groups on adjacent carbon atoms. The G protein is eluted from the column with the addition of 500 mM Tris buffer. The APBA pool containing G protein is then dialyzed and applied to a hydroxyapatite column (Type II, 80 μm) and eluted with an increase in potassium phosphate concentration. The hydroxyapatite column pool containing G-protein is dialyzed and applied to a lectin (wheat germ) affinity chromatography column and eluted with 300 mM N-acetyl-glucosamine.

Figure 1:
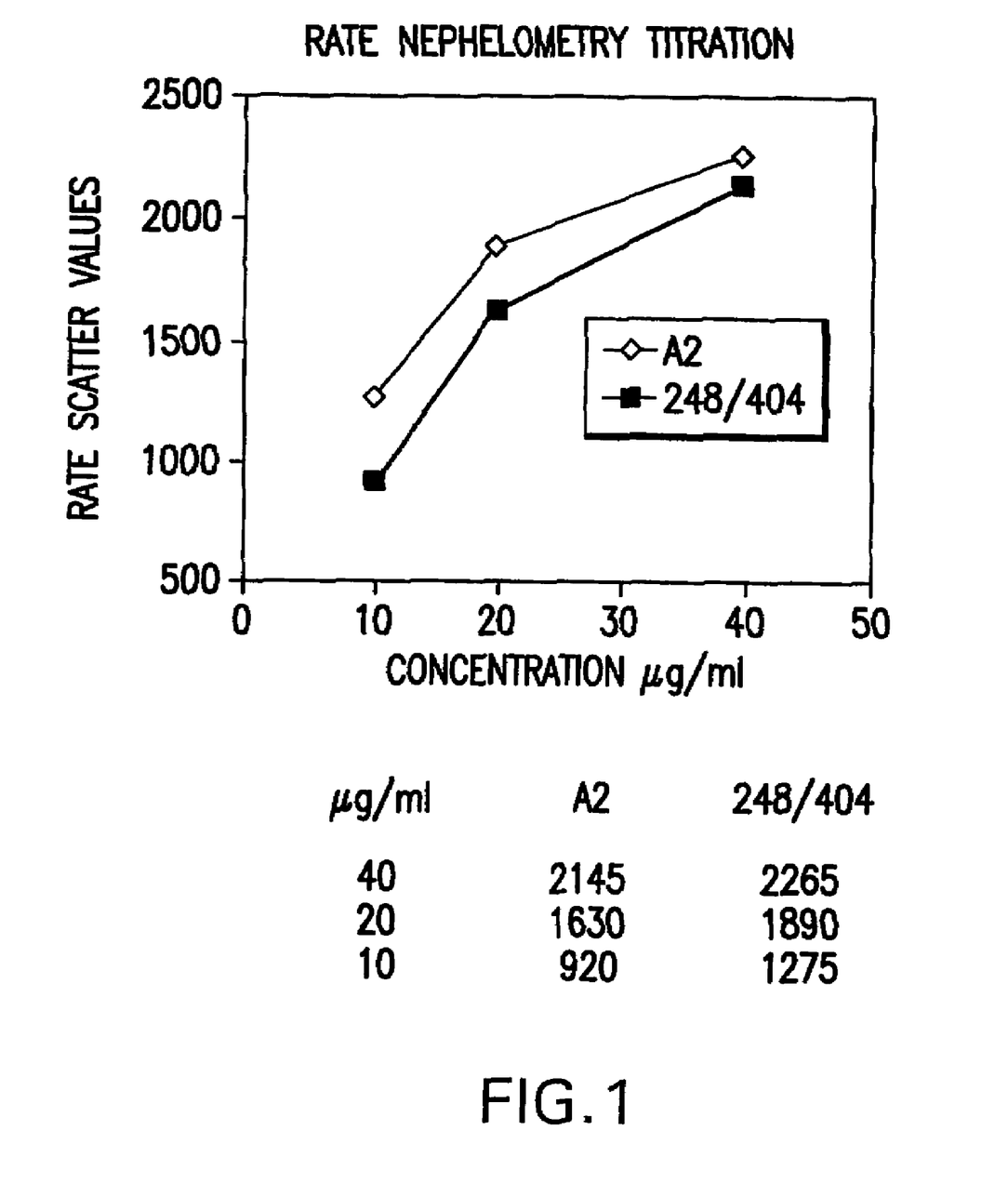
FIG. 1 shows rate nephelometry titration of PFP-2 and PFP-3 when using a mixture of polyclonal antibodies made against PFP-2.

Various immunological and biochemical assays were employed to compare the F proteins from the mutant virus strain (cpts-248/404, PFP-3) and the parent strain (A2, PFP-2). From an immunological standpoint, no statistically significant differences were observed. The antigenicity of the two proteins was determined by both rate nephelometry and competition ELISAs using monoclonal antibodies and human convalescent sera. Rate nephelometry, which quantifies the rate of change in molecular size as an antigen/antibody complex forms, was similar between the two proteins when using a mixture of polyclonal antibodies made against PFP-2 (FIG. 1). The conservation of B cell epitopes between the two proteins was evaluated by competitive ELISA. In those studies, the ability of PFP-2 and PFP-3 to inhibit the binding of seven different monoclonal antibodies or a mixture of polyclonal antibodies to either the homologous or heterologous protein adsorbed to the ELISA plate (Tables 1 and 2) was compared. It should be noted that all these monoclonal antibodies have previously been shown to neutralize virus infectivity. It was found that PFP-3 caused greater than 95% inhibition of the monoclonal antibodies to PFP-2 and PFP-3. Similarly, PFP-2 caused >80% inhibition and in most cases >93% inhibition of the monoclonal antibodies to PFP-3 and PFP-2. This is strong evidence that these major B cell epitopes, which represent regions of the molecule that can stimulate protective antibody responses, are conserved between the two proteins, even though there are minor differences in their secondary structures (see below).

The immunogenicity and efficacy of the two F proteins in a BALB/c mouse model were evaluated. The data (Table 3) suggest that the systemic humoral immune responses induced by either protein when adsorbed to $Al(OH)_3$ are equivalent. Moreover, the immunity engendered by either protein protects the lower respiratory tract of BALB/c mice against experimental infection with RSV to the same degree.

Figure 2:
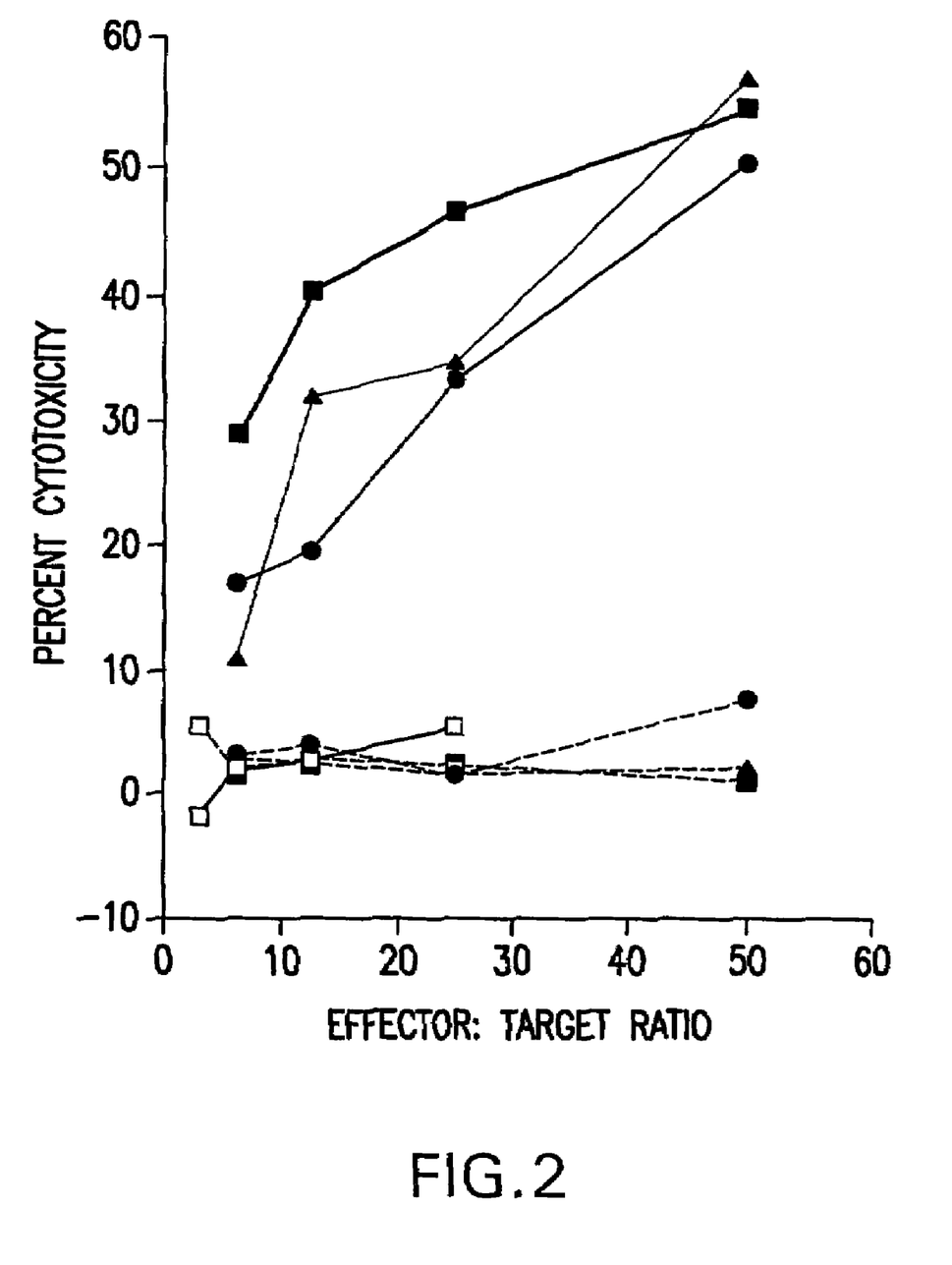

To evaluate the ability of the two F proteins to induce cell-mediated immune responses, mice were immunized with protein formulated with STIMULON™ QS-21 adjuvant (Antigenics, Framingham, Mass.) (QS-21) and the induction of virus-specific killer cells was measured by an in vitro cytolytic assay. The data indicate that the systemic cell-mediated immune responses generated after immunization with either PFP-2 or PFP-3 were equivalent (FIG. 2). The data with QS-21 further show that the two proteins were able to generate equivalent systemic humoral immune responses (Table 4) along with equivalent complement-assisted and complement-independent neutralizing antibody titers in a two-dose immunization schedule (Table 4).

Various biochemical assays were employed to compare the primary, secondary, tertiary, and quaternary structures of the two proteins along with any differences in their glycosylation patterns. As might be expected from chemical mutagenesis and subsequent attenuation, PFP-3 displays four amino acid substitutions in its primary sequence, two in the $F_1$ and two in the $F_2$ polypeptides. Two changes result in a charge change, one change is to proline, and the other change is very conservative (Table 5). Circular dichroism analysis indicates that PFP-3 contains more beta-sheet structure than does PFP-2 (data not shown). The aggregation state of the two purified bulks, as measured by analytical ultracentrifugation and multi-angle laser light scattering (MALLS) appeared to be similar, with the proteins existing as aggregates >500 kD in molecular weight (data not shown). Various SDS-PAGE conditions, i.e. heated vs. nonheated, and reduced vs. nonreduced, displayed similar banding patterns between PFP-3 and PFP-2 of dimeric, trimeric, and oligomeric structure (data not shown), all of which have been implicated in the usefulness of the protein as an immunogenic composition. PFP-3 $F_1$ and $F_2$ polypeptides both display apparent smaller molecular weights than their PFP-2 counterparts by SDS-PAGE analysis. Carbohydrate analysis, utilizing fluorescence-activated carbohydrate electrophoresis (FACE), reveals subtle differences in the sialic acid, mannose, and fucose content of the N-linked carbohydrates (data not shown).

In summary, it has been shown that even though subtle physico-chemical differences between the two molecules were found to exist, PFP-2 and PFP-3 are antigenically and immunologically equivalent.

TABLE 1

A2 vs. 248/404 - Monoclonal Competitive ELISA
Percent Inhibition

| Monoclonal Antibody | A2 Binding Assay | | 248/404 Binding Assay | |
|---|---|---|---|---|
| | A2 (Homo) | 248/404 (Hetero) | A2 (Hetero) | 248/404 (Homo) |
| L4 | 97.5 | 94.6 | 98.8 | 97.3 |
| A5 | 98.4 | 93.8 | >99 | 99.0 |
| 133-1H | 98.1 | 93.1 | >99 | 96.2 |
| 143-6C | 98.4 | 95.0 | >99 | 98.1 |
| 1129 | >99 | 94.7 | >99 | 95.9 |
| 1269 | 96.6 | 82.3 | >99 | >99 |
| 1243 | >99 | 94.4 | >99 | 98.9 |

TABLE 2

A2 vs. 248/404 - Polyclonal Competitive ELISA
Percent Inhibition

| | A2 Binding Assay | | 248/404 Binding Assay | |
|---|---|---|---|---|
| Sera | A2 (Homo) | 248/404 (Hetero) | A2 (Hetero) | 248/404 (Homo) |
| C587645 (pooled human) | 95.5 | 93.9 | 77.9 | 87.0 |
| C587769 (pooled human) | 96.8 | 92.5 | 75.2 | 85.6 |
| Control C (individual) | 94.0 | 93.4 | 85.4 | 80.7 |
| Control D (individual) | 97.1 | 94.6 | 77.1 | 83.8 |

TABLE 3

A2 vs. 248/404
The systemic humoral and protective immune responses of BALB/c mice 4 weeks after primary immunization with PFP-2 and PFP-3 (T97-0156)
MEAN ANTIBODY TITERS[1]

| F Protein (Dose) | Anti-F Protein (×1000) | | | Neutralizing | | GMT RSV $(\log_{10})^2$ |
|---|---|---|---|---|---|---|
| | IgG | IgG1 | IgG2a | +C' | −C' | |
| (248/404) (3000 ng) | 145.1[a] | 86.9[a] | 1.4 | 20 | <20 | 2.1 ± 1.0 |
| (248/404) (300 ng) | 52.0[b] | 18.8[a] | <0.1 | <20 | <20 | 2.5 ± 1.2 |
| (248/404) (30 ng) | 14.5[c] | 10.7[c] | <0.1 | <20 | <20 | 3.7 ± 0.5 |
| A2 (3000 ng) | 122.3[d] | 75.8[d] | 1.1 | <20 | <20 | 2.8 ± 0.9 |
| A2 (300 ng) | 66.0[e] | 28.6[e] | <0.1 | <20 | <20 | 2.6 ± 1.2 |
| A2 (30 ng) | 27.9 | 15.1 | <0.1 | <20 | <20 | 2.6 ± 1.1 |
| RSV (A2) | 159.3 | 8.9 | 26.5 | 78 | <20 | <1.4 ± 0.1 |
| PBS | <1.0 | <0.1 | <0.1 | <20 | <20 | 4.4 ± 1.0 |

[1]BALB/c mice were primed with the indicated doses of fusion (F) protein from either the A2 or 248/404 strains of RSV. The proteins were adsorbed to aluminum hydroxide (AlOH) adjuvant. Control mice were injected with AlOH in PBS alone, or were infected with the A2 strain of RSV. Four weeks after primary vaccination sera were collected for the determination of geometric mean endpoint anti-F protein total and subclass IgG antibody titers by ELISA. Neutralizing antibody titers were also revealed by the plaque reduction neutralization test against A2 strain of virus in the presence (+)and absence (−) of 5% complement. There were 5 mice per group.
[2]The geometric mean titers (GMT) of RSV are expressed per gram of pulmonary tissue. The titers were determined 4 days after challenge with the A2 strain of RSV.
[a]P < 0.05 when compared to sera from mice vaccinated with either 300 or 30 ng F protein from strain 248/404. P > 0.05 when compared to sera from mice vaccinated with 3000 ng F protein from strain A2.
[b]P < 0.05 when compared to sera from mice vaccinated with 30 ng F protein from strain 248/404. P > 0.05 when compared to sera from mice vaccinated with 300 ng F protein from strain A2.
[c]P < 0.05 when compared to sera from mice vaccinated with 30 ng F protein A2 strain.
[d]P < 0.05 when compared to sera from mice vaccinated with either 300 or 30 ng F protein strain A2.
[e]P < 0.05 when compared to sera from mice vaccinated with either 30 ng F protein from strain 248/404 or 300 ng F protein from strain A2
[f]P > 0.05 when compared to sera from mice vaccinated with 30 ng F protein from strain A2.

TABLE 4

The systemic humoral immune responses of BALB/c
mice 2 and 4 weeks after primary and secondary
immunization with PFP-2 and PFP-3 (T97-2502).
GEOMETRIC MEAN ANTIBODY TITERS ($Log_{10}$)[2]

|  | Anti-F Protein | | | Neutralizing | |
|---|---|---|---|---|---|
| PRIMARY | IgG | IgG1 | IgG2a | +C' | −C' |
| F Protein (248/404) | 5.7 ± 0.1 | 4.9 ± 0.1 | 4.9 ± 0.1 | 2.5 ± 0.4 | <1.3 |
| F Protein (A2) | 6.1 ± 0.1[a] | 5.3 ± 0.1[a] | 5.3 ± 0.1[a] | 2.7 ± 0.4[b] | 1.4 ± 0.2 |
| RSV (A2) | 4.8 ± 0.1 | 3.6 ± 0.3 | 4.1 ± 0.1 | 2.1 ± 0.3 | <1.3 |
| PBS (QS-21) | <1.7 | <1.7 | <1.7 | <1.3 | <1.3 |
| SECONDARY | IgC | IgG1 | IgG2a | +C$^2$ | −C$^2$ |
| F Protein (248/404) | 7.1 ± 0.1 | 6.2 ± 0.1 | 6.1 ± 0.1 | 3.6 ± 0.2 | 2.7 ± 0.2 |
| F Protein (A2) | 7.0 ± 0.1[b] | 6.1 ± 0.1[b] | 6.0 ± 0.1[b] | 3.7 ± 0.2[b] | 3.0 ± 0.3[b] |
| RSV (A2) | 5.7 ± 0.4 | 4.3 ± 0.3 | 5.2 ± 0.1 | 3.3 ± 0.4 | 2.6 ± 0.5 |
| PBS (QS-21) | <1.7 | <1.7 | <1.7 | <1.3 | <1.3 |

[1]BALB/c mice were vaccinated on weeks 0 and 4 with 3 μg F protein from either the 248/404 or A2 strains of RSV. The F protein was formulated with 20 μg QS-21. There were 5 mice per group.
[2]The geometric mean antibody titers were determined on sera collected 2 and 4 weeks after primary and secondary vaccination respectively. Endpoint IgG and neutralizing antibody titers were determined by ELISA and the plaque reduction neutralization test respectively. The latter antibody titers were determined in the presence (+) and absence (−) of 5% complement ($C^1$).
[a]P < 0.05 when compared to sera from mice vaccinated with F Protein from strain 248/404.
[b]P > 0.05 when compared to sera from mice vaccinated with F Protein from strain 248/404.

TABLE 5

A2 vs. 248/404
Sequence Differences in F-Protein

| Nucleotide Position | Amino Acid Position | A2 (M6) | cpts-248/404 | Charge Change |
|---|---|---|---|---|
| 5857 | 66 | Lys (K) | Glu (E) | −2 |
| 5962 | 101 | Gln (Q) | Pro (P) | 0 |
| 6313 | 218 | Glu (E) | Ala (A) | +1 |
| 7228 | 523 | Thr (T) | Ile (I) | 0 |

Preparation and Use of the Immunogenic Composition

Immunogenic compositions may be prepared from the F protein (PFP-3) of RSV as disclosed herein. The immunogenic composition elicits an immune response that produces antibodies, including anti-RSV and anti-F antibodies. Such antibodies may be viral neutralizing and/or anti-fusion antibodies.

Immunogenic compositions may be prepared as injectables, as liquid solutions, suspensions or emulsions. The active immunogenic ingredient or ingredients may be mixed with pharmaceutically acceptable excipients that are compatible therewith. Such excipients may include water, saline, dextrose, glycerol, ethanol, and combinations thereof. The immunogenic compositions may further contain auxiliary substances, such as wetting or emulsifying agents, pH buffering agents, or adjuvants to enhance the effectiveness thereof. The immunogenic compositions may be administered parenterally, by injection subcutaneously, intradermally or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active immunogenic ingredient (s) in the range of about 0.5 to about 10%, such as about 1 to 2%. Oral formulations may include normally employed carriers, such as pharmaceutical grades of saccharine, cellulose and magnesium carbonate. These compositions can take the form of solutions, suspensions, tablets, pills, capsules, sustained release formulations or powders and contain about 1 to 95% of the active ingredient(s), such as about 20 to about 75%. The immunogenic preparations are administered in a manner compatible with the dosage formulation, and in such amount as will be therapeutically effective, immunogenic and protective. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art. Suitable regimes for initial administration and booster doses are also variable, but may include an initial administration followed by subsequent booster administrations. The dosage may also depend or the route of administration and will vary according to the size of the host.

The concentration of the active ingredient protein in an immunogenic composition according to the invention is in general about 1 to 95%. An immunogenic composition that contains antigenic material of only one pathogen is a monovalent composition. Immunogenic compositions that contain antigenic material of several pathogens are polyvalent (combination) compositions and also within the scope of the present invention. Such polyvalent compositions contain, for example, material from various pathogens (such as PIV-1, PIV-2 and/or PIV-3) or from various strains of the same pathogen, or from combinations of various pathogens.

In certain embodiments, the immunogenic composition will comprise one or more adjuvants. As defined herein, an "adjuvant" is a substance that serves to enhance the immunogenicity of an immunogenic composition of this invention.

Thus, adjuvants are often given to boost the immune response and are well known to the skilled artisan.

Preferred adjuvants to enhance effectiveness of the composition include, but are not limited to:

(1) aluminum salts (alum), such as aluminum hydroxide, aluminum phosphate, aluminum sulfate, etc.;

(2) oil-in-water emulsion formulations (with or without other specific immunostimulating agents such as muramyl peptides (see below) or bacterial cell wall components), such as, for example, (a) MF59 (PCT Publ. No. WO 90/14837), containing 5% Squalene, 0.5% Tween 80, and 0.5% Span 85 (optionally containing various amounts of MTP-PE (see below, although not required)) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% Squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(3) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(4) bacterial lipopolysaccharides, synthetic lipid A analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy4-O-phosphono-3-O-[(R)-3-tetradecanoyloxytetradecanoyl]-2-[(R)-3-tetradecanoyloxytetradecanoylamino]-b-D-glucopyranoside, which is also know as 529 (formerly known as RC529), which is formulated as an aqueous form or as a stable emulsion, synthetic polynucleotides such as oligonucleotides containing CpG motif(s) (U.S. Pat. No. 6,207,646);

(5) cytokines, such as interleukins (e.g., IL-1, IL-2, IL-4, IL-5, IL-6, IL-7, IL-12, IL-15, IL-18, etc.), interferons (e.g., gamma interferon), granulocyte magrophage colony stimulating factor (GM-CSF), macrophage colony stimulating factor (M-CSF), tumor nucrosis factor (TNF), etc.;

(6) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an $E.\ coli$ heat-labile toxin (LT), particularly LT-K63, LT-R72, CT-S109, PT-K9/G129 (see, e.g., WO 93/13302 and WO 92/19265); and (7) other substances that act as immunostimulating agents to enhance the effectiveness of the composition.

As mentioned above, muramyl peptides include, but are not limited to, N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE), etc.

RSV subunit immunogenic compositions will provide a strategy for immunization of high-risk children, adults, and the elderly against RSV-induced lower respiratory tract disease.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Dulbecco's Modification of Eagles Medium (DMEM) and fetal bovine serum (FBS), with or without Pluronic F68, culture medium was used for cell culture and virus growth. The cells used in these Examples were qualified African green monkey kidney cells (VERO) obtained from Wyeth's Master Cell Bank. The RS virus used was the RSV mutant subgroup A2 strain cpts-248/404 (ATCC VR 2454), which was obtained from the National Institute of Allergy and Infectious Diseases (NIAID), Bethesda, Md., where it was developed (U.S. Pat. No. 5,922,326, incorporated herein by reference).

Example 1

This Example illustrates the screening method utilized to identify attenuated strains of RSV capable of producing high yields of RSV fusion (F) protein in VERO cell microcarrier cultures.

A VERO cell culture was initiated from frozen ampoules of Wyeth's qualified Working Cell Bank. The ampoules were thawed and inoculated into cell factories (Nunc) for the initial stage. The cells were grown at 37° C.±0.5° C. without $CO_2$. The media used for cell cultivation was DMEM supplemented with 10% (v/v) FBS. Two 100% media exchanges were performed for optimal cell growth. Upon confluency, cells were released from the surface by treatment with trypsin and inoculated onto Cytodex 1 microcarriers in a 3.6-L (working volume) bioreactor equipped with an environmental control. The cells were cultivated in the bioreactor under controlled conditions until greater than 90% confluency ($3\text{-}4\times10^6$ cells/mL) was reached. The cells were infected with an attenuated RSV A2 strain at a multiplicity of infection (MOI) of 0.001. Harvest was performed eight days post-infection, when greater than 90% syncytial formation and cell detachment from the microcarriers were achieved. Harvest samples containing microcarriers were frozen at −70° C. for analysis of RSV F protein concentration using an F protein specific monoclonal antibody (L4) in a capture ELISA format. Frozen harvest retention samples were thawed at room temperature and 25 μL of 10% Triton X-100 non-ionic detergent was added to 500 μL of thawed sample in an Eppendorf tube for solubilization of the F protein. Samples were placed on a rotating rocker at slow speed for 1 hour at 15-30° C. The microcarriers were allowed to settle and the supernatant was transferred to an L4-coated 96-well microtiter plate containing an F protein standard. After a one-hour incubation at room temperature, the wells were washed and probed with a primary antibody (Rabbit anti-F-protein). After a one-hour incubation at room temperature, the wells were washed and probed with a secondary antibody (Goat anti-Rabbit HRP). After a one-hour incubation at room temperature, the wells were washed and probed with Horseradish Peroxidase Enzyme Substrate (ABTS). Color development proceeded for 30 minutes and plates were read at a wavelength of 405 nm. A standard curve was fitted to a log-cubic equation using the optical density (OD) values from the F protein standard. The concentration of F protein from the unknown attenuated RSV strain was determined by averaging all consecutive OD values that coincide within the range of OD values used for the standard curve. By this method, strains of RSV capable of producing at least a five-fold increase in RSV F protein yields as compared with the parent A2 strain were identified. See Tables 6 and 7 below.

TABLE 6

RSV Strains Screened for Increased F Protein Levels

| RSV Strain | Average F-Protein Level* (μg/mL) |
|---|---|
| A2 (parent) (PFP-2) | 5.0 |
| cpts248/404 (PFP-3) | 22.0 |
| RSS-2 | 6.5-11 |
| Cp52 (B-strain) | 0.57 |
| RA2cp248/404 | 13.2 |
| rA2cp248/404/ΔSH | 7.6 |
| rA2cp248/404/1030 | 20.1 |
| rA2cp248/404/1030/ΔSH | 4.1 |
| rA2cpΔNS2 | 1.1 |
| rA2cp248/404/ΔNS2 | 1.5 |
| rA2cp530/1009/ΔNS2 | 1.7 |
| rA2cp530/1009/404 | 1.0 |
| rABcp248/404/1030 | 1.0 |
| rABcp248/404/ΔSH | 1.8 |
| RABcp530/1009/ΔNS2 | 0.6 |
| rABcp248/404/ΔNS2 | 1.9 |
| rABcpΔNS2 | 0.5 |
| ts 1c 9097C-99 | 9.5 |

*Value is average from preseed production, master virus seed, and/or clinical production.

Example 2

This Example illustrates the production of RSV on a mammalian cell line on microcarriers in a 30-L controlled bioreactor.

A VERO cell culture was initiated from frozen ampoules of Wyeth's qualified Working Cell Bank (BB-MF 6735) at passage 134. The ampoules were thawed and inoculated into 6000 $cm^2$ cell factories (Nunc) for the initial stage at a cell density of $2\pm0.5\times10^4$ cells/$cm^2$. The cells were grown at 37° C.±0.5° C. without $CO_2$. The media used for cell cultivation was DMEM supplemented with 10% (v/v) FBS. Two 100% media exchanges were performed for optimal cell growth. Upon confluency, cells were released from the surface by treatment with trypsin and inoculated onto Cytodex 1 microcarriers at $0.5\text{-}0.8\times10^6$ cells/mL in a 3.6-L (working volume) bioreactor equipped with an environmental control. The cells were cultivated in the bioreactor under controlled conditions until greater than 90% confluency ($3\text{-}4\times10^6$ cells/mL) was reached. Cells were then trypsinized off the microcarriers and scaled up into a 23-L (working volume) bioreactor. VERO cells were cultivated in the bioreactor under controlled conditions until greater than 90% confluency ($3\text{-}4\times10^6$ c/mL) was reached. The media used for initial cell cultivation in both bioreactors was DMEM with 5% (v/v) FBS. Following a one- to two-day period of batch-wise cell growth, the culture was perfused with DMEM with 1% (v/v) FBS for three to six culture volume exchanges. The following parameters were monitored and/or controlled cell growth, glucose (>1 g/L) and glutamine (2-4 mM), dissolved oxygen (50%), pH (7.4) and temperature (37° C.). At 90% confluency the bioreactor temperature was reduced to 30±0.5° C. and perfusion was turned off while all other environmental conditions were maintained. When the temperature equilibrated to 30±0.5° C., cells were infected with the qualified RSV subgroup A2 strain cpts-248/404 virus seed at a multiplicity of infection (MOI) of 0.001. Perfusion remained off for 24±5 hours to allow virus adsorption and a batch addition of glucose and glutamine was made (to reach 3 g/L glucose and 4 mM glutamine). Perfusion was then continued during infection for up to 4 days. Harvest was performed eight days post-infection, when greater than 90% syncytial formation and cell detachment from the microcarriers were achieved. Further processing of the harvested material is described in Example 3.

Example 3

This Example illustrates the process of purifying subunit RSV PFP-3 from a viral concentrate, Sterile lysis buffer [10% (v/v) Triton-X-100 in PBS, pH 7.4±0.1] was added to the bioreactor to a final detergent concentration of 0.5% (v/v). The culture was agitated during the lysis period of 2-3 hours at 30±0.5° C. At the end of lysis in situ, the microcarriers were allowed to settle and the lysed culture supernatant was clarified through a Seitz® 700 (6-15 μm) cellulose depth filter (0.3 $ft^2$/L harvest) followed by a Seitz® 100 (1-3 μm) cellulose depth filter (0.3 $ft^2$/L harvest). The clarified supernatant was aseptically transferred to a holding vessel for storage at 2-8° C. prior to purification.

The clarified viral harvest was concentrated five- to 10-fold using either spiral wound or plate-and-frame ultrafiltration (0.5 $ft^2$/L original harvest) and diafiltered with about 10 volumes of 75 mM Tris-Cl, 0.1% Triton X-100, pH 8 (>100 L) utilizing a 30K Amicon spiral wound, regenerated cellulose or PALL Centrasette Omega® polyethersulfone module. The diafiltered lysate was applied to an anion exchange column (DEAE Sepharose or MacroPrep) equilibrated with 75 mM Tris-Cl, 0.1% Triton X-100, pH 8, and the flow through fraction containing the F-protein was collected. The flow-through fraction was concentrated about two-fold using either spiral wound or plate-and-frame ultrafiltration (0.3 $ft^2$/L original harvest) and diafiltered with about 10 volumes of 20 mM sodium acetate, 100 mM NaCl, 0.1% Triton X-100, pH 4 (approximately 70 L) utilizing either a 30K Millipore spiral wound PrepScale®, polyethersulfone or PALL Centrasette Omega® polyethersulfone module, and then applied to a cation exchange column (CM Sepharose FF). The F protein was eluted with a step gradient to 350 mM NaCl.

The cation exchange pool was concentrated about two-fold using either spiral wound or plate-and-frame ultrafiltration (0.05 $ft^2$/L original harvest) and diafiltered with about 10 volumes of 10 mM $KPO_4$, pH 6 (approximately 25 L) utilizing either a 30K Millipore spiral wound PrepScale®, polyethersulfone or PALL Centramate Omega® polyethersulfone module, and applied to a hydroxyapatite column (Type II, 80 μM) equilibrated with 10 mM $KPO_4$, 0.1% Triton X-100, pH 6. The F protein was eluted with a step gradient to 150 mM $KPO_4$, 0.1% Triton X-100, pH 7. Fractions containing F protein were pooled, terminally sterile-filtered, and frozen at −70° C. until formulation.

The F protein bulk was analyzed by SDS-PAGE and found to be ≧90% pure.

TABLE 7

Comparison of PFP-3 purification process utilizing cpts-248/404 or the parent A2 strain.

| | A2 | cpts-248/404 |
|---|---|---|
| Multiplicity of Infection (MOI) | 0.001 | 0.001 |
| F-Protein @ Harvest (μg/mL) | 5.3 | 22.4 |
| Virus Titer (pfu/mL) @ Harvest | $4\times10^7$ | $2\times10^8$ |

TABLE 7-continued

Comparison of PFP-3 purification process utilizing cpts-248/404 or the parent A2 strain.

| | A2 | cpts-248/404 |
|---|---|---|
| Cell Concentration (cells/mL) @ Infection | $3 \times 10^6$ | $3 \times 10^6$ |
| F Protein Recovery (%) | 25 | 25 |
| F-Protein Recovery (mg/L harvest) | 1.0 | 5.6 |
| 50 μg Doses/L harvest | 20 | 110 |

Example 4

This Example illustrates the immunogenicity of a PFP-3 immunogenic composition in RSV seropositive children with cystic fibrosis.

In a phase II, multi-center, adjuvant-controlled trial, 151 children received the adjuvant control (aluminum phosphate) and 143 received the PFP-3 immunogenic composition. The F protein accounted for over 95% of the total viral protein content in the immunogenic composition and the G protein for less than 2%. Children randomized to receive the PFP-3 immunogenic composition received a 0.5 ml dose containing 30 μg of PFP-3 and 0.5 mg of aluminum phosphate (0.125 mg dose of aluminum), while children in the adjuvant-control group received a 0.5 ml dose containing 0.5 mg of aluminum phosphate (0.125 mg of aluminum). The immunogenic compositions were administered intramuscularly in the deltoid or lateral thigh. Blood samples were obtained at pre-immunization, 28 days post-immunization and end-of-study and assayed for neutralizing antibodies (Nt Ab) and binding antibodies (Bd Ab) to the F protein.

Tests for Nt Ab to RSV subgroups A (RSV/A) and B (PSV/B) were performed by a microneutralization assay in 96 well microtiter plates with HEp-2 cells as previously described (Piedra P. A., Glezen W. P., Kasel J. A., et al. "*Immunogenic composition* 1995; 13:1095-1101, 1995; Groothuis J. R., King S. J., Hogerman D. A., et al." *J. Infect. Dis.*, 177:467-469, 1998). An enzyme-linked immunosorbent assay (ELISA) was used to measure serum IgG binding antibodies (Bd Ab) to the F (ELISA-F) and G (ELISA-G) proteins as previously described. A rise in Ab titer by four folds or greater is considered a significant antibody response. Comparing the percentage of children in the adjuvant-control and PFP-3 immunogenic composition groups who experienced a four-fold or greater rise in Ab titer at 28 days post-immunization, it was found that nearly all (97%) had a four-fold or greater ELISA-F Bd Ab rise compared to 1 % of the adjuvant-control cohort. A significant Nt Ab rise to RSV/A and RSV/B was observed in 67% and 55% of the PFP-3 immunized children compared to 2% and 3%, respectively, of the adjuvant-control cohort (Table 8 below).

TABLE 8

Immunogenicity of the PFP-3 immunogenic composition

| Test | Interval | Adjuvant control | PFP-3 | P Value |
|---|---|---|---|---|
| RSV/A (GMT log 2) | Pre-immunization | 5.5 ± 1.5* | 5.4 ± 1.6 | 0.49 |
| | 28 days post-immunization | 5.5 ± 1.6 | 7.9 ± 1.8 | <0.001 |
| RSV/A (≧4-fold rise) | 28 days post-immunization | 3/150 (2%) | 96/143 (67%) | <0.001 |
| RSV/B (GMT log 2) | Pre-immunization | 6.5 ± 2.3 | 6.4 ± 2.4 | 0.82 |
| | 28 days post-immunization | 6.6 ± 2.3 | 8.4 ± 1.9 | <0.001 |
| RSV/B (≧4-fold rise) | 28 days post-immunization | 4/149 (3%) | 78/143 (55%) | <0.001 |
| ELISA-F (GMT log 2) | Pre-immunization | 13.2 ± 1.6 | 13.1 ± 1.7 | 0.49 |
| | 28 days post-immunization | 13.1 ± 1.7 | 17.9 ± 1.2 | <0.001 |
| ELISA-F (≧4-fold rise) | 28 days post-immunization | 2/149 (1%) | 139/143 (97%) | <0.001 |
| ELISA-G (GMT log 2) | Pre-immunization | 9.0 ± 1.9 | 9.1 ± 1.6 | 0.58 |
| | 28 days post-immunization | 8.8 ± 1.9 | 9.3 ± 1.6 | 0.01 |
| ELISA-G (≧4-fold rise) | 28 days post-immunization | 1/149 (1%) | 4/143 (3%) | 0.21 |

*serum geometric mean antibody titer in log 2 and standard deviation
RSV/A = neutralizing antibody to RSV/A;
RSV/B = neutralizing antibody to RSV/B;
ELISA-F = binding antibody to F protein;
ELISA-G = binding antibody to G protein.
Comparisons between categorical variables were conducted using the Chi-square test or Fisher's exact test for expected cell counts less than 5, and the two-sample t test was used for continuous variables.

The invention claimed is:

1. A method of identifying an attenuated respiratory syncytial virus (RSV) strain that produces high yields of RSV surface glycoprotein F when compared with the parent A2 strain, which method comprises:
   providing a eukaryotic cell culture;
   infecting the eukaryotic cell culture with a live, attenuated RSV strain at 30° C.;
   harvesting the infected cell culture;
   solubilizing the F protein in the harvested culture; and
   subsequently determining the glycoprotein F concentration in the harvested culture,
   wherein at least a five-fold increase in glycoprotein F concentration produced when the attenuated RSV strain is grown in the cell culture at 30° C. is an indication that the attenuated RSV strain produces high yields of RSV F glycoprotein when compared with the parent A2 strain grown at 37° C.

2. The method of claim 1, wherein the identified attenuated RSV strain is the RSV mutant strain cpts-248/404.

3. The method of claim 1, wherein the eukaryotic cell culture is a VERO, MRC-5, FRhL, CEF or PER.C6 cell culture.

4. The method of claim 1, wherein the solubilizing comprises adding detergent to the harvested culture.

* * * * *